(12) United States Patent
Etminan

(10) Patent No.: US 11,234,839 B2
(45) Date of Patent: Feb. 1, 2022

(54) DEVICE FOR IMPLEMENTING INTERVERTEBRAL FUSION

(71) Applicant: Mohammad Etminan, Houston, TX (US)

(72) Inventor: Mohammad Etminan, Houston, TX (US)

( * ) Notice: Subject to any disclaimer, the term of this patent is extended or adjusted under 35 U.S.C. 154(b) by 0 days.

(21) Appl. No.: 16/880,101

(22) Filed: May 21, 2020

(65) Prior Publication Data

US 2020/0368034 A1 Nov. 26, 2020

Related U.S. Application Data

(60) Provisional application No. 62/850,702, filed on May 21, 2019.

(51) Int. Cl.
*A61F 2/44* (2006.01)
*A61F 2/30* (2006.01)

(52) U.S. Cl.
CPC .......... *A61F 2/447* (2013.01); *A61F 2/30771* (2013.01); *A61F 2/442* (2013.01); *A61F 2002/3055* (2013.01); *A61F 2002/30571* (2013.01); *A61F 2002/30574* (2013.01); *A61F 2002/30884* (2013.01)

(58) Field of Classification Search
CPC ...... A61F 2/447; A61F 2/30771; A61F 2/442; A61F 2002/3055; A61F 2002/30571; A61F 2002/30574; A61F 2002/30884
USPC ........................................... 623/17.11–17.16
See application file for complete search history.

(56) References Cited

U.S. PATENT DOCUMENTS

| | | | | |
|---|---|---|---|---|
| 8,070,813 B2* | 12/2011 | Grotz | .................... | A61F 2/4611 623/17.11 |
| 8,083,800 B2* | 12/2011 | Edie | .................... | A61F 2/44 623/17.16 |
| 8,241,363 B2* | 8/2012 | Sommerich | ........... | A61F 2/4611 623/17.16 |
| 2003/0191531 A1* | 10/2003 | Berry | ........................ | A61F 2/44 623/17.11 |
| 2007/0255421 A1* | 11/2007 | Dickson | .................... | A61F 2/44 623/23.47 |
| 2008/0161933 A1* | 7/2008 | Grotz | .................... | A61F 2/4465 623/17.16 |
| 2008/0281424 A1* | 11/2008 | Parry | .................... | A61F 2/4455 623/17.16 |
| 2009/0138083 A1* | 5/2009 | Biyani | ...................... | A61F 2/44 623/17.11 |
| 2009/0270987 A1* | 10/2009 | Heinz | .................... | A61F 2/441 623/17.16 |
| 2010/0274357 A1* | 10/2010 | Miller | ........................ | A61F 2/44 623/17.16 |
| 2011/0208310 A1* | 8/2011 | Aschmann | ................ | A61F 2/44 623/17.16 |
| 2016/0106551 A1* | 4/2016 | Grimberg, Jr. | ........ | A61F 2/4601 623/17.16 |

\* cited by examiner

*Primary Examiner* — Jessica Weiss
(74) *Attorney, Agent, or Firm* — Ostrolenk Faber LLP (57) ABSTRACT

An interbody support system that includes a support and a containment body, the containment body having a fixed height or an adjustable height, and the support having a support column, which may have a fixed height or an adjustable height, an inferior plate at one end of the support column and a superior plate at the other end of the support column.

14 Claims, 11 Drawing Sheets

DEVICE FOR IMPLEMENTING INTERVERTEBRAL FUSION

CROSS REFERENCE TO RELATED APPLICATIONS

The present application claims priority to U.S. Provisional Application Ser. No. 62/850,702, filed May 21, 2019, the entire disclosure of which is incorporated by reference herein.

FIELD OF INVENTION

The present invention relates to a device and a system for implementing intervertebral fusion following corpectomy.

BACKGROUND

Cervical, thoracic, or lumbar corpectomy procedures are performed in cases of significant deformity of the vertebral body. That is, when the degree of neural compression is such that removing the cervical disc is no longer sufficient to address the pathology. In such instances, a portion (e.g. the central portion) of an affected vertebra is removed (corpectomy) to allow appropriate correction of the alignment and decompression of the spinal cord. The procedure does not require removal of the entire anterior portion of the vertebra. There will be portions of the vertebra that will remain on the sides, or anteriorly depending on the approach and technique used.

Anterior cervical corpectomy (ACC) is an example of a medical procedure that can address cervical spinal stenosis and myelopathy by removing an osteophyte (bone spur) from a vertebra that is pressing on the spinal cord.

Figure 1A:
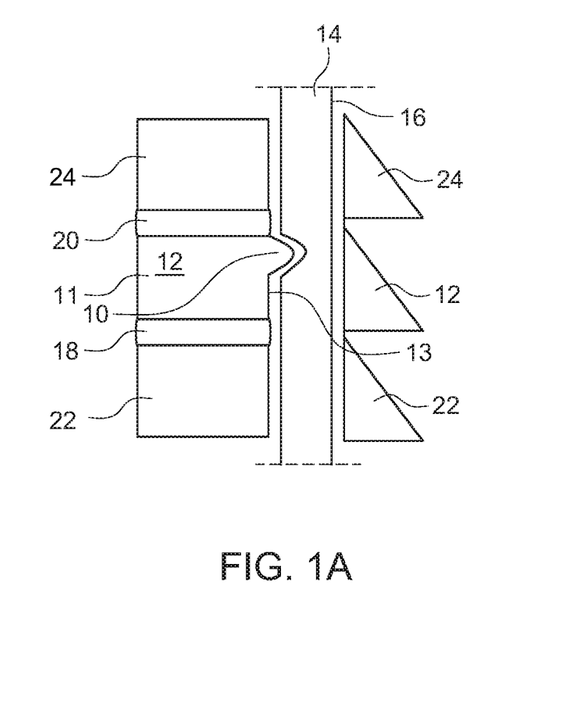
FIG. 1A shows a side view of a portion of the spinal column and FIG. 1B shows an anterior view thereof.

Referring to FIG. 1A which is provided for illustrative purposes, a bone spur 10 projecting from the interior side of a vertebra 12, that faces and is closest to the spinal cord 14, can press against the spinal cord 14 inside of the spinal cord cavity 16. The ACC procedure can remove the bone spur 10 to relieve the nerve compression.

Figure 1B:
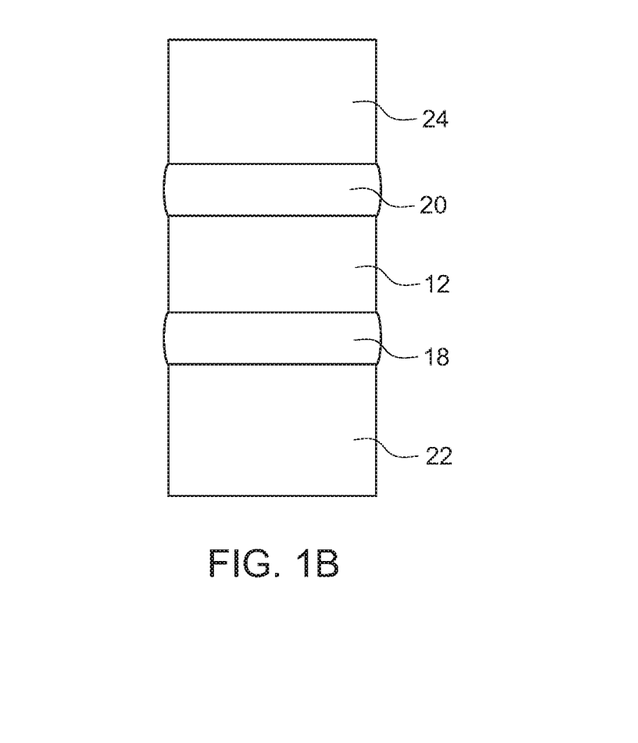
Figure 1C:
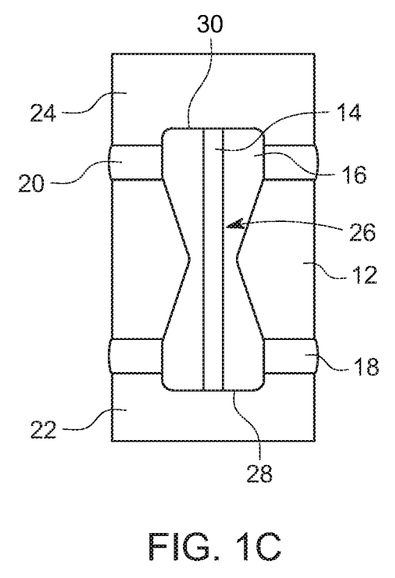
FIG. 1C shows the anterior view shown in FIG. 1B after corpectomy.

FIGS. 1A and 1B illustrate the vertebra 12, which is adjacent an inferior disk 18 and a superior disk 20. The inferior disk 18 is adjacent an inferior vertebra 22, and the superior disk 20 is adjacent a superior vertebra 24. In order to reach and remove the bone spur 10, a vertical channel 26 (as seen in FIG. 1C) must be cut in the vertebra 12, which channel would extend from the anterior surface 11 of the vertebra 12 to the posterior surface 13 thereof. The channel 26 would remove the bone spur 10.

The ACC procedure would further require the removal of at least a portion of the superior disk 20 above the channel 26 to reach the superior vertebra 24 and the removal of a portion of the inferior disk 18 below the channel 26 to reach the inferior vertebra 22. End plates 28, 30 are then prepared in the inferior vertebra 22 and the superior vertebra 24 by the removal of some of the bone from each vertebrae 22, 24. Each end plate 28, 30 may be a recess formed in a vertebra 22, 24.

ACC is typically followed by a procedure that promotes fusion of at least the inferior vertebra 22 and the superior vertebra 24. To promote fusion, bone graft material is placed in the channel 26 to extend from the end plate 28 to the end plate 30. A plate spanning, and connected to, anterior surfaces of the three vertebrae 12, 22, 24 can be employed for stability while the grafting works.

It should be noted that FIGS. 1A-1C are directed at a corpectomy which results in a channel 26 that reaches the interior surface 13 of vertebra 12 and the spinal cord cavity 16 in order to remove the bone spur 10. It should be noted that the channel 26 does not need to extend from one end plate 28 to another 30, but may extend from one end plate 28, or 30 to a location in vertebra 12.

There are many different fusion techniques including structural allograft (possibly fibula, tibia, or calcaneus), static cage placement or expandable cage placement.

Figure 2:
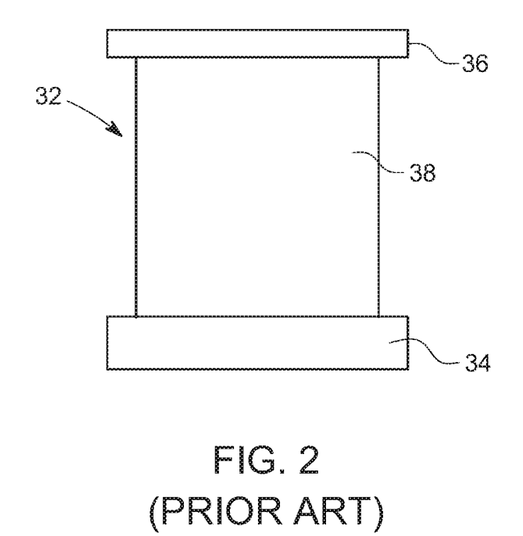
FIG. 2 shows a prior art cage design.

When used, an expandable cage is placed in position and expanded to reach the end plates 28, 30. An example of such a cage 32 is illustrated in FIG. 2, which includes two oppositely disposed support plates 34, 36 and a central column 38 connected to, and supporting the support plates 34, 36. The central column 38 is telescopically expandable, whereby its height may be adjusted once it is in place. As can be seen, the transverse cross-section of the central column 38 and the area of support plates 34, 36 are nearly the same, which means most of the channel 26 will be occupied by the column 38.

Furthermore, because the channel 26 extends to the spinal cord 14, it is not possible to deposit graft material around the central column 36, while it may be possible to deposit graft material inside of the column 36 (if it is a hollow cylinder) to extend between the end plates 28, 30.

It is assumed that, once the graft material is deposited, new bone will form from the superior and the inferior endplates and will travel towards the center, eventually resulting in a bony union. This model often results in failure of fusion due to the distance that the bony material has to travel, the challenged healing environment, and the small fusion area present. In the expandable cage model, the cage (central column 38) is packed with grafting material before expansion. After the cage is implanted, the cage is expanded, which increases the volume inside of the cage. Thus, more grafting material will need to be placed inside of the cage. This task can be difficult and ineffective.

SUMMARY

The present application proposes a different method of achieving fusion.

1. The application discloses an expandable/static intervertebral support design with:
    a. a small central core (This is contrary to the current art that emphasizes a large central core), and
    b. an emphasis on,
        i. the fusion outside of the central core lateral to the central core through fenestration of the end plate foot print,
        ii. the bony ingrowth due to the materials chosen for the end plate, and
        iii. the placement of the bone lateral to the implant to take advantage of remaining bone mass.
2. Also, disclosed is a graft containment (e.g. slides/shims/stops/Clips), that
    a. mates or is an integral part of the central strut (column) of the support, and is stabilized with a variety of technique,
    b. allows packing of graft material, and
    c. protects neural structures from the packed graft material.

The supports disclosed herein permit increasing the fusion rate, easing the insertion and the removal of the support due to the use of less metal or other materials.

An interbody support system according to the present invention is insertable in a channel defined in a vertebra and includes a support having a central column, an inferior support plate at one end of the support column having a contact surface, and a superior support plate at another end of the support column having a contact surface, the system further including a containment body extending at least between the inferior support plate and the superior support plate.

The support column may be height-adjustable or may have a fixed height.

Through openings may be defined in the inferior support plate and the superior support plate.

An outrigger may be attached to each support plate.

The surface area of the contact surface of the inferior support plate and the surface area of the contact surface of the superior support plate may be each at least twice the transverse cross-sectional area of the support column.

The containment body may be a height-adjustable curtain, or a curtain that has a fixed height.

The containment body may be detachably attached to the support, for example, to the support plates, or may be fixed to the support plates.

The containment body may be a clip having an anterior wall and two sidewalls, each sidewall extending from a respective edge of the anterior wall, and formed, for example, as a leaf spring. A flange may extend laterally away from each sidewall. A wing portion may extend at an angle away from each flange. Each sidewall of the clip may include a depression sized and shaped to make surface to surface contact with the support column, or the sidewalls of the clip may be formed to correspond to an exterior shape of the support column.

Outriggers in the form of projections may be formed on the sidewalls of the clip, holes or slots may be formed in the sidewalls and the anterior wall of the clip, or a slug may be formed on the anterior wall of the clip. The slug may include a hole therein.

Other features and advantages of the present invention will become apparent from the following description of the invention which refers to the accompanying drawings.

DETAILED DESCRIPTION

Figure 3A:
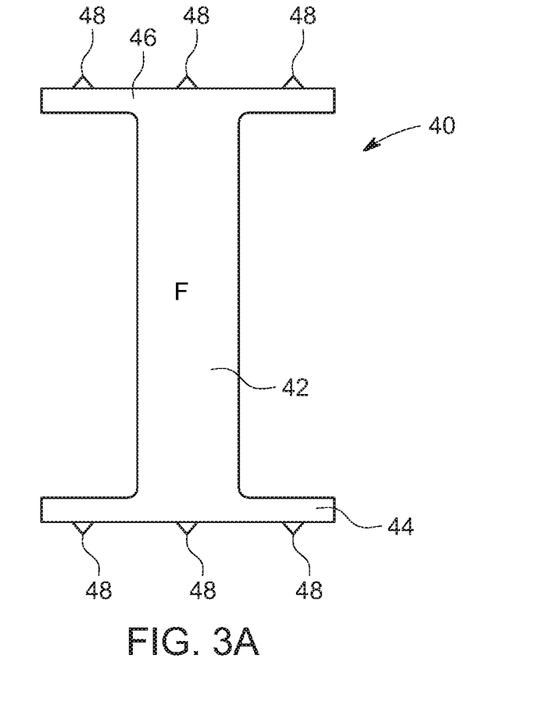
FIG. 3A shows a first embodiment of a support according to the present invention.

FIG. 3A depicts a side view of an intervertebral support 40 according to the first embodiment of the present invention. The support 40 includes a support column 42 with a fixed height, an inferior support plate 44 and a superior support plate 46. The column 42 and the support plates 44, 46 may be independent and discrete bodies that are integrated with one another (for example, by using threaded surfaces to screw into one another), or may be formed as a unitary body. Column 42 may be cylindrical or any suitable shape. The support plates 44, 46 may be circular or any suitable shape. Each plate 44, 46 may have serrations 48 (e.g. teeth) to anchor into the end plates 28, 30 when the support 40 is in place. While not shown, each support plate 44, 46 has through openings (e.g. circular or rectangular openings) therein to permit the graft material to reach the end plates 28, 30 when the graft material is placed around the support column 42 and between the plates 44, 46.

Figure 3B:
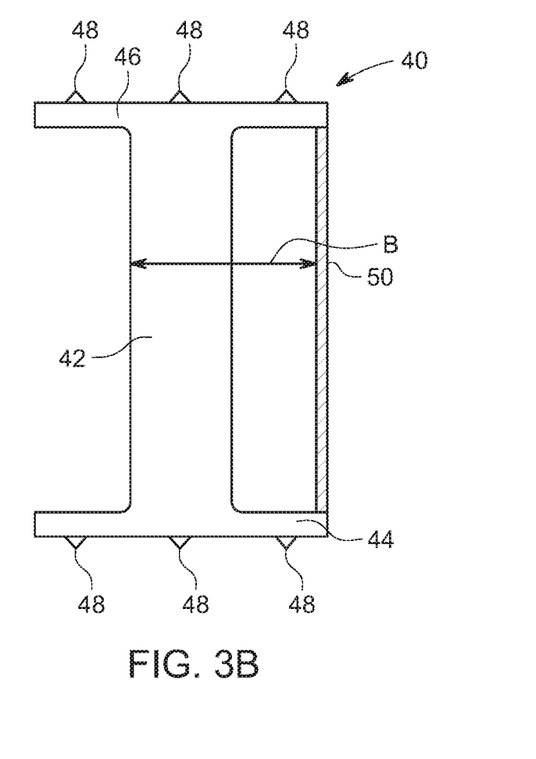
FIG. 3B shows a second embodiment of a support according to the present invention.

When there has been a corpectomy, the graft material could reach the spinal cord 14. In this case, and according to another embodiment of the present invention, a curtain 50 may be provided at the side of the support 40 that is closest to the spinal cavity 16. The curtain 50, which may be detachably attached to the support 40 (e.g. to the plates 44, 46) or fixed to the support 40 (e.g. to the plates 44, 46) will be arranged to block at least the open part of the channel 26 that is at the interior surface 13 of the vertebra 12 to prevent encroachment of the graft material into the spinal cavity 16. The curtain 50 may be flat, or may be curved (for example, when the plates 44, 46 are circular).

Figure 4A:
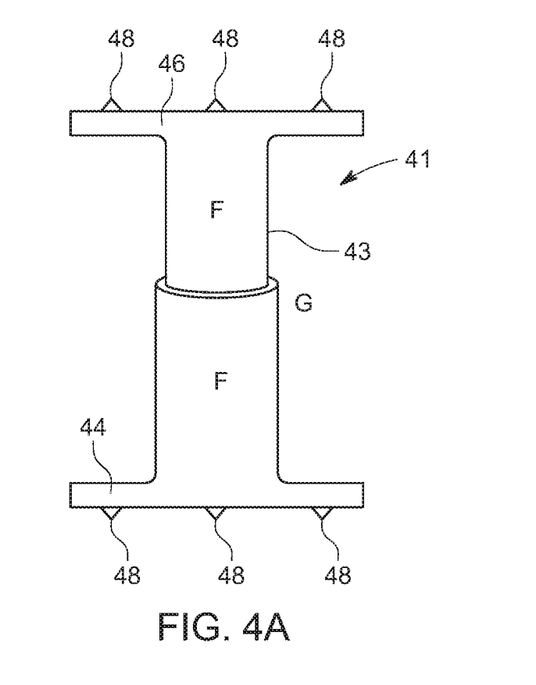
FIG. 4A shows a third embodiment of a support according to the present invention.

Referring to FIG. 4A, in a support 41 according to the third embodiment, instead of the column 42, which has a fixed height, a height-adjustable column 43 may be used. The adjustability may be implemented in any suitable manner. For example, a jack screw type adjustable mechanism may be used.

Figure 4B:
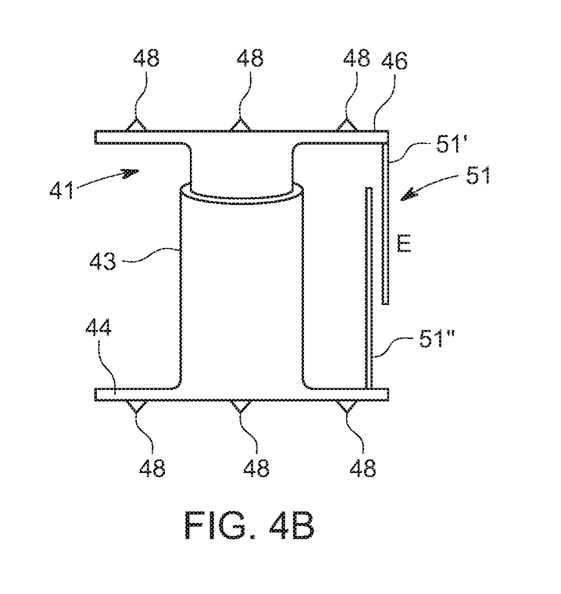
FIG. 4B shows a fourth embodiment of a support according to the present invention.

Referring to FIG. 4B, in a support according to the fourth embodiment, a height-adjustable curtain 51 may be used with a support 41 to block the encroachment of the graft material when the support 41 is used in a channel 26 defined by corpectomy. The curtain 51 may include two or more flat bodies 51', 51" that are vertically movable relative to one another or two or more curved bodies that are vertically movable relative to one another. Each flat body 51', 51" may be fixed to the support (e.g. fixed to plates 44, 46) or detachably attached to the support 41 (e.g. to the plates 44, 46).

A narrow, fixed or expandable column (strut) 41 or 43 allows for the use of smaller and more easily workable insertion tools because there will be a larger working space not occupied by critical neural and vascular structures. The surface area of the surfaces of the plates 44, 46 that make contact with the end plates 28, 30 and/or are connected to the support column 42 or 43 should be at least twice the transverse cross-sectional area of the column 42 or 43, regardless of whether the column 42 or 43 is a tube (i.e. has a hollow interior) or is a rod (i.e. has a solid interior). That is, the transverse cross-sectional area covers the area bounded by the exterior surface of the column 42 or 43, and may include a region or regions where there is no solid material.

Figure 5A:
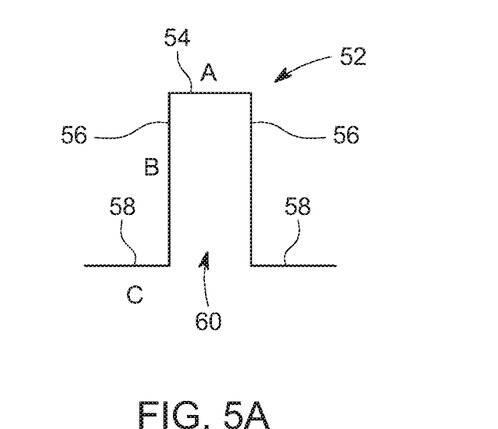
FIG. 5A shows a top view of a clip in a fifth embodiment and FIG. 5B shows a perspective view of the clip of FIG. 5A.
Figure 5B:
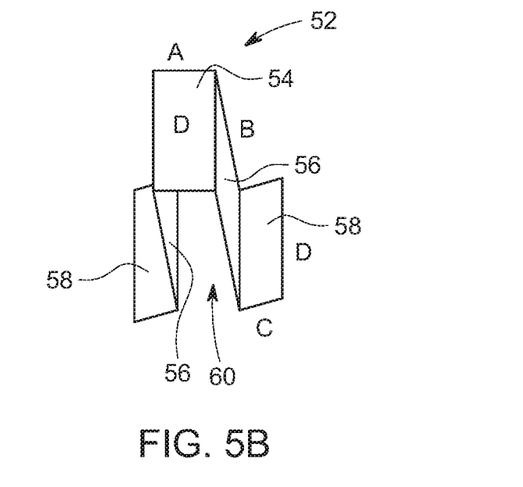

Referring to FIGS. 5A and 5B, in a fifth embodiment, instead of a curtain 50 or 51 to provide graft material containment, a clip 52 may be used to provide the graft material containment. The clip 52 may be a unitary body that includes an anterior wall 54 that would have its exterior surface face the anterior opening of channel 26 when installed. Two spaced side walls 56 extend from the anterior wall 54 each from a respective edge of the anterior wall 54 and each terminates at a respective flange 58 that extends laterally away from a respective edge of a respective side wall 56. The clip 52 defines a space 60 in which at least the column 42 or the column 43 of a support would be received and the flanges 58 would make intimate and direct contact with the sidewalls of the channel 26 in the vertebra 12 under the spring force of sidewalls 56 acting as leaf springs. The side walls 56 may include openings (e.g. circular, rectangular, or any other suitable shape) therein to permit mating of insertion instruments for placement of clip 52 on column 41 or 43.

Figure 5C:
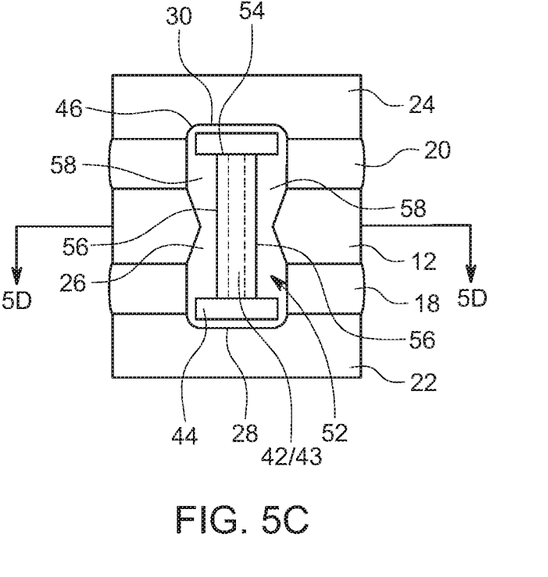
FIG. 5C shows an interior view of a clip installed around a support according to the present invention.
Figure 5D:
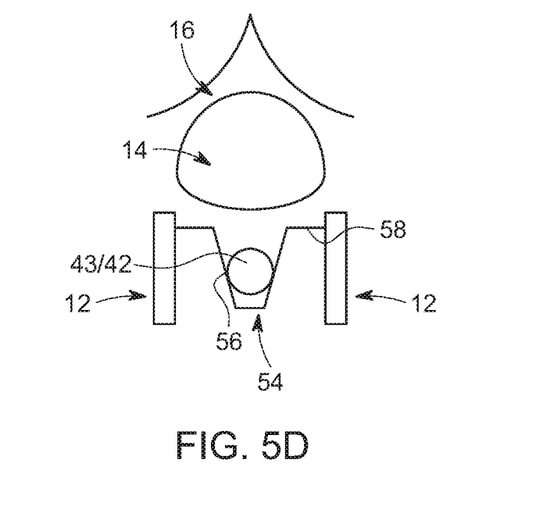
FIG. 5D shows a cross-sectional view along line 5D-5D in FIG. 5C and viewed in the direction of the arrows.

Referring to FIGS. 5C and 5D, when clip 52 is installed in place, column 42 or 43 is received in the space 60, the exterior surface of the anterior wall 54 faces the anterior opening of the channel 26, the sidewalls 56 extend from the anterior wall 54 toward the posterior opening of the channel 26, and the flanges 58 extend to and make direct contact with the sidewalls of the channel 26. Once the clip 52 is installed, there will be enough space between the clip 52 and the sidewalls of the channel 26 for any graft material deposited in the channel to make direct contact with the sidewalls of the channel 26 as well as the endplates 28, 30.

Figure 5E:
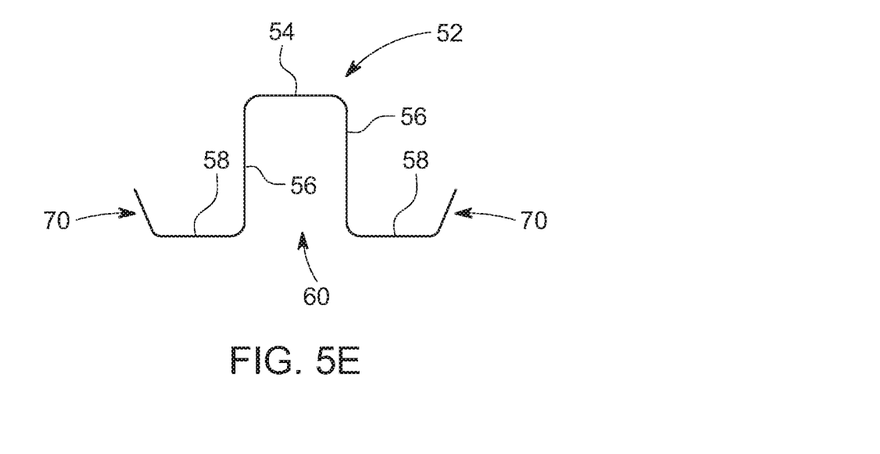
FIG. 5E shows a second embodiment of the clip.

Referring to FIG. 5E, the clip 52 may have a wing portion 70 extending from a distal edge of each flange 58 preferably parallel to sidewalls 56, or at least away from the posterior opening of the channel 26 for a portion of the way, defining a cup-shaped body at each lateral side of the clip 52 to allow for better protection of neural elements.

Figure 5F:
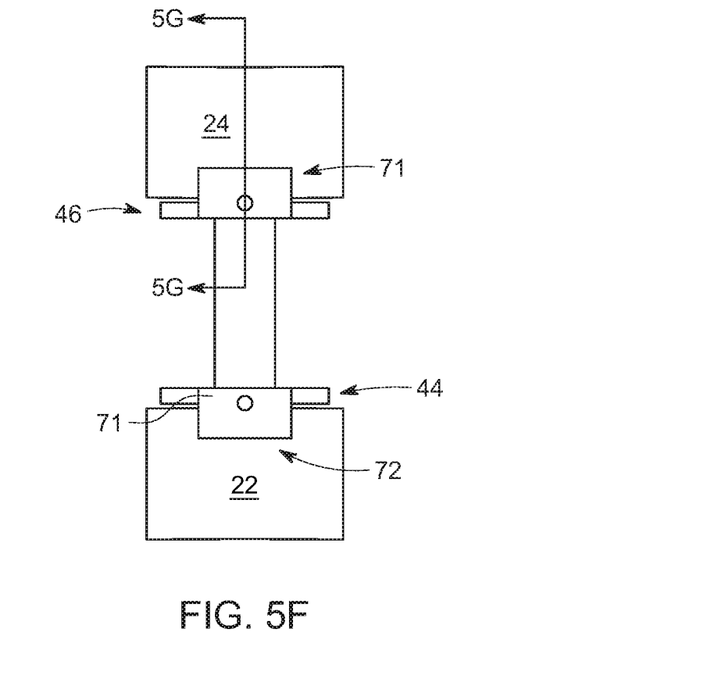
FIG. 5F shows an anterior view of an embodiment in which outriggers are used to prevent migration of the support toward the spinal cord cavity.
Figure 5G:
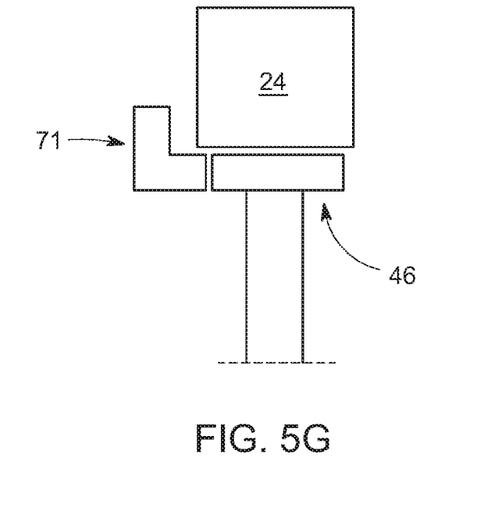
FIG. 5G is a cross-sectional view along line 5G-5G viewed in the direction of the arrows.

There may be temporary fixation (e.g. a screw) or permanent fixation (e.g. a screw) through the support plate 44 or the support plate 46 to allow for the fixation of the support plate(s) onto the vertebral end plate. Referring to FIG. 5F, according to another embodiment, one or more outriggers 71, 72 may be attached temporarily with a screw or the like to the support plates 44, 46 to engage the anterior surfaces of the vertebra 22 and vertebra 24. The outriggers 71, 72 may be formed as plates with various depths to prevent posterior migration of the support 40 or 41 toward the spinal cord 14 during the placement of the clip 52. Each outrigger may cover the whole width of a support plate 44 or 46 or a portion thereof. It may be temporarily fixed with screws or other fixation techniques.

Figure 5H:
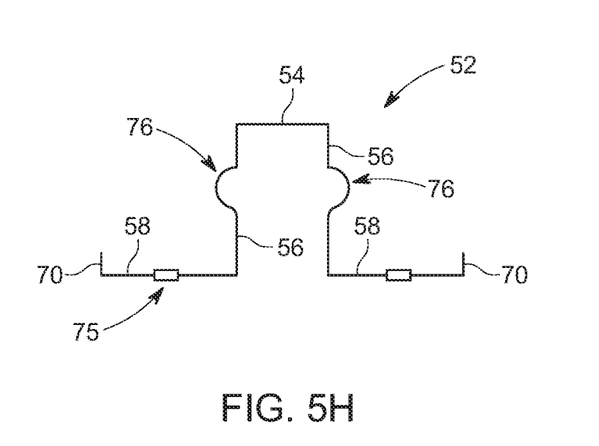
FIGS. 5H-5N show the third, the fourth, the fifth, the sixth, the seventh, the eight and the ninth embodiments of the clip.

The anterior wall 54 may be deformed/shaped to mimic the shape of the column 42 or 43 or may not. Referring to FIG. 5H, each sidewall 56 of the clip 52 may include a depression 76 formed therein which is sized and shaped to make surface to surface contact with the column 42, 43 to further stabilize the clip 52.

Figure 5I:
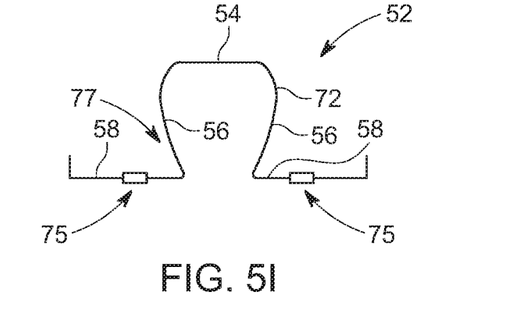

Referring to FIG. 5I, the sidewalls 56 of the clip 52 may be formed to correspond to the outer shape of the column 42, 43 to couple to the column 42, 43 better. For example, instead of flat sidewalls 56, the sidewalls may be curved sidewalls 77.

The clip may be modified to include appendages or holes to allow for the insertion, removal, and fixation of the clip. These modifications will allow for the appropriate interaction of the insertion tool(s) and the removal tool(s) with the clip 52. They will also allow for the stabilization of the clip relative to the columns 42, 43. The modifications may be made to any surface of the clip 52.

Figure 5J:
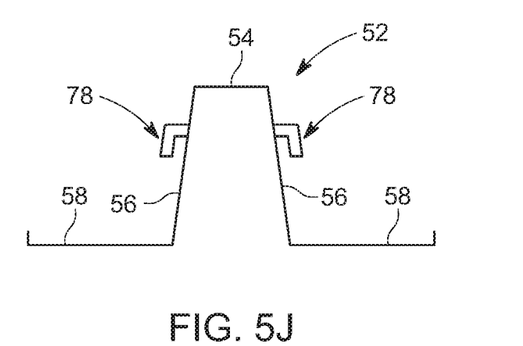

Referring to FIG. 5J, the sidewalls 56 of the clip 52 may include outriggers 78 in the form of projections on the exterior surfaces thereof to allow better engagement with an insertion tool or a removal tool.

Figure 5K:
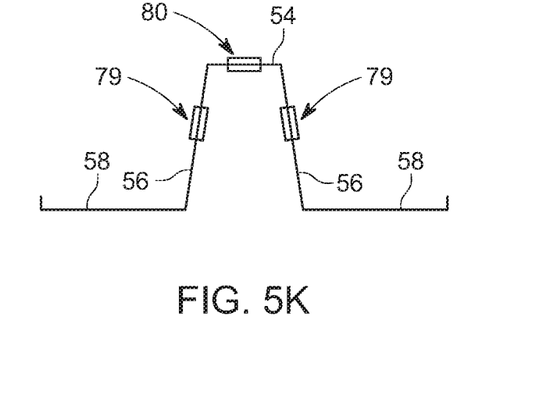

Referring to FIG. 5K, instead of or in addition to outriggers 78, holes or slots 79, 80 may be provided on the anterior wall 54 or the sidewalls 56 of the clip 52 to allow engagement with the insertion tool or the removal tool.

Figure 5L:
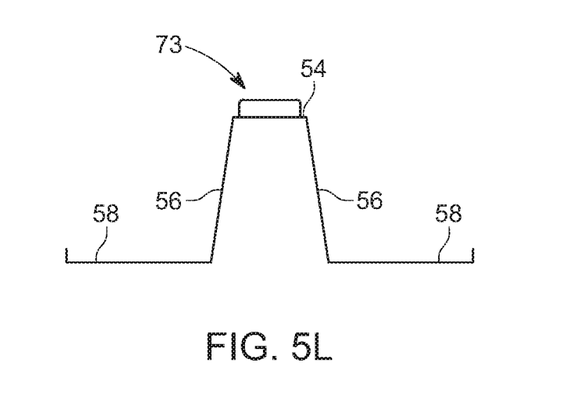
Figure 5M:
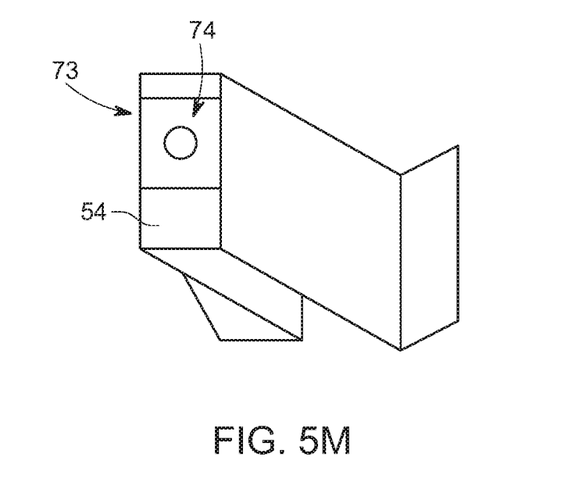

Referring to FIG. 5L, the anterior wall 54 may have a modification 73 in the form of a slug or the like to allow manipulation of the clip 52 (for example, for position adjustment) with a tool. The slug 73 may include a hole 74, which may be threaded. The hole 74 may be aligned with another hole in the anterior wall 54 to prevent using a screw to fix the clip to the column 42 or 43.

Figure 5N:
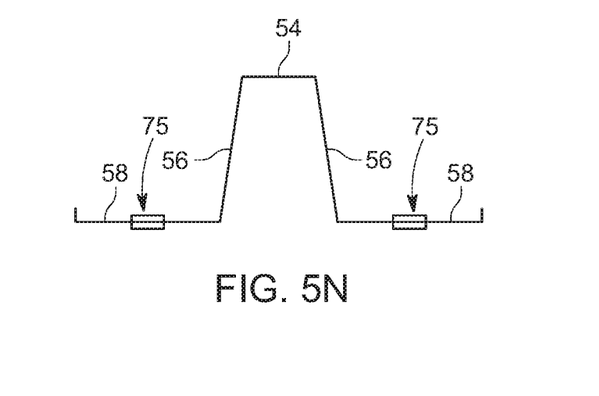
Figure 6:
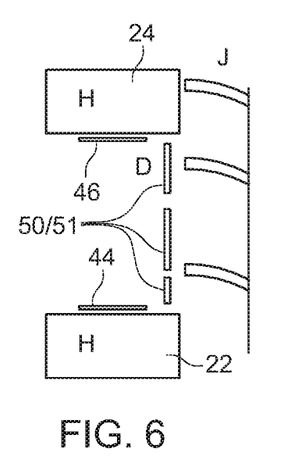
FIG. 6 shows the positioning of the plates and the containment without showing the column or the vertebra.
Figure 7A:
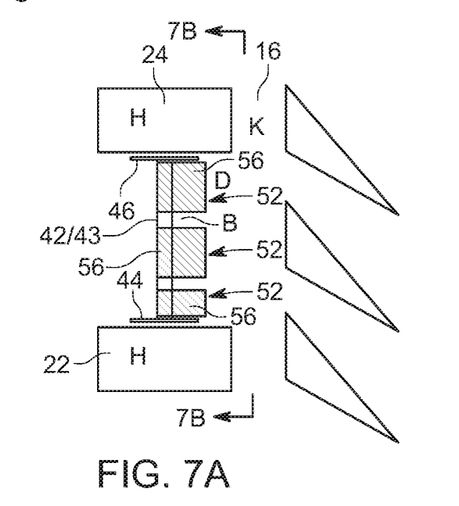
FIG. 7A shows a side view with the central vertebra removed from view and at least one containment body (showing three) arranged between the support plates.
Figure 7B:
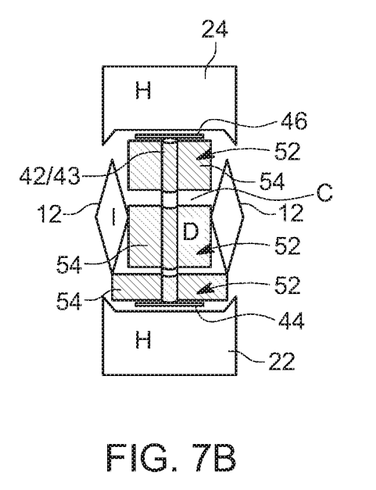
FIG. 7B shows a view of the arrangement shown in FIG. 7A with the central vertebra viewed in the direction of the arrow 7B.

Referring to FIG. 5N, the flanges 58 may include a modification 75 (e.g. a hole, a slit, or an extension) to allow for manipulation of the clip with a tool (e.g. for position adjustment).

The transverse cross-section of column 42 or 43 may have a variety of different shapes including a circle (i.e. a cylinder), a rectangle or a square, an ellipse, or any combination of shapes. Also, the transverse cross-section may have a uniform cross-section along the length of the column 42 or 43 or a variable cross-section. The column 42 or 43 may have regions of variable stiffness along its length and thus may have regions of increased rotational stiffness/stability in the form of areas of increased material deposition/placement.

The column 43 may interdigitate with possible design features (i.e. reinforcements) to increase rotational stability of the strut.

To implement the procedure, first a support 40 or 41 is placed in the region prepared through corpectomy (as described above using FIGS. 1A-1C as illustrations).

In the case of corpectomy, after the placement of a support 40 or 41, access to the spinal cavity 16 is blocked by using a curtain (50 or 51) or curtains (50 or 51), a clip 52 or a plurality of clips 52 for the purpose of containing the graft material before depositing the graft material around the support column and in direct contact with the channel 26 sidewalls and the end plates 28, 30.

A height-adjustable support is advantageous because it can be adjusted to the right height in the body. It is preferred to place the clip or clips after the in vivo implantation of the support 41 with the height-adjustable column 43 instead of outside the body in the operating room.

Although the present invention has been described in relation to particular embodiments thereof, many other variations and modifications and other uses will become apparent to those skilled in the art. It is preferred, therefore, that the present invention be limited not by the specific disclosure herein, but only by the appended claims.

What is claimed is:

1. An interbody support system insertable in a channel defined in a vertebra, comprising: a support having a support column; an inferior support plate at one end of the support column having a contact surface; a superior support plate at another end of the support column having a contact surface; and the system further including a containment body extending at least between the inferior support plate and the superior support plate, wherein the containment body is a clip having an anterior wall and two sidewalls, each sidewall extending from a respective edge of the anterior wall and formed as a leaf spring.

2. The interbody support system of claim 1, wherein the support column is height-adjustable.

3. The interbody support system of claim 1, wherein a surface area of the contact surface of the inferior support plate and a surface area of the contact surface of the superior support plate is each at least twice a transverse cross-sectional area of the support column.

4. The interbody support system of claim 1, further comprising through openings defined in the inferior support plate and the superior support plate.

5. The interbody support system of claim 1, further comprising an outrigger attached to the superior support plate and an outrigger attached to the inferior support plate.

6. The interbody support system of claim 1, wherein each sidewall of the clip includes a depression sized and shaped to make surface to surface contact with the support column.

7. The interbody support system of claim 1, wherein the sidewalls of the clip are formed to correspond to an exterior shape of the support column.

8. The interbody support system of claim 1, further comprising holes or slots formed in the sidewalls and the anterior wall of the clip.

9. The interbody support system of claim 1, further comprising a flange extending laterally away from each sidewall.

10. The interbody support system of claim 9, wherein the flanges include holes, slits, or extensions.

11. An interbody support system insertable in a channel defined in a vertebra, comprising: a support having a support column; an inferior support plate at one end of the support column having a contact surface; a superior support plate at another end of the support column having a contact surface; a containment body extending at least between the inferior support plate and the superior support plate, wherein the containment body is a clip having an anterior wall and two sidewalls, each sidewall extending from a respective edge of the anterior wall; a flange extending laterally away from each sidewall and a wing portion extending at an angle away from each flange.

12. An interbody support system insertable in a channel defined in a vertebra, comprising: a support having a support column; an inferior support plate at one end of the support column having a contact surface; a superior support plate at another end of the support column having a contact surface; a containment body extending at least between the inferior support plate and the superior support plate, wherein the containment body is a clip having an anterior wall and two sidewalls, each sidewall extending from a respective edge of the anterior wall, and further comprising outriggers in the form of projections formed on the sidewalls of the clip.

13. An interbody support system insertable in a channel defined in a vertebra, comprising: a support having a support column; an inferior support plate at one end of the support column having a contact surface; a superior support plate at another end of the support column having a contact surface; a containment body extending at least between the inferior support plate and the superior support plate, wherein the containment body is a clip having an anterior wall and two sidewalls, each sidewall extending from a respective edge of the anterior wall, and further comprising a slug formed on the anterior wall of the clip.

14. The interbody support system of claim 13, wherein the slug includes a hole therein.

\* \* \* \* \*